(12) United States Patent
Sato et al.

(10) Patent No.: US 9,068,812 B2
(45) Date of Patent: Jun. 30, 2015

(54) IMAGING APPARATUS, IMAGING METHOD, AND STORAGE MEDIUM

(71) Applicant: CANON KABUSHIKI KAISHA, Tokyo (JP)

(72) Inventors: Makoto Sato, Tokyo (JP); Tomoyuki Makihira, Tokyo (JP); Yoshihiko Iwase, Kyoto (JP); Kazuhide Miyata, Yokohama (JP); Hiroyuki Shinbata, Tama (JP); Ritsuya Tomita, Kawasaki (JP); Daisuke Kibe, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 66 days.

(21) Appl. No.: 13/743,851

(22) Filed: Jan. 17, 2013

(65) Prior Publication Data
US 2013/0188139 A1     Jul. 25, 2013

(30) Foreign Application Priority Data

Jan. 20, 2012   (JP) ................................. 2012-010278

(51) Int. Cl.
  *A61B 3/10*     (2006.01)
  *A61B 3/14*     (2006.01)
  *G01B 9/02*     (2006.01)

(52) U.S. Cl.
  CPC ............ *G01B 9/02091* (2013.01); *A61B 3/102* (2013.01); *A61B 3/14* (2013.01); *G01B 9/02064* (2013.01); *G01B 9/0203* (2013.01); *G01B 9/02027* (2013.01); *G01B 2290/70* (2013.01); *G01B 2290/45* (2013.01)

(58) Field of Classification Search
  CPC ....... A61B 3/102; A61B 3/12; G01B 9/02064
  USPC ......................................................... 351/215
  See application file for complete search history.

(56) References Cited

U.S. PATENT DOCUMENTS

2006/0215172 A1 *   9/2006   Abe .............................. 356/497
2009/0153876 A1 *   6/2009   Chan et al. .................... 356/521
(Continued)

FOREIGN PATENT DOCUMENTS

CN          1924633 A      3/2007
WO        2010122118 A     10/2010
(Continued)

OTHER PUBLICATIONS

Hitzenberger, et al., "Quantitative measurement of the degree of polarization uniformity of light backscattered by retinal layers by polarization sensitive OCT", Proc. of SPIE, (2009), pp. 716814-1-716814-5, vol. 7168.

*Primary Examiner* — Jordan Schwartz
(74) *Attorney, Agent, or Firm* — Canon USA Inc. IP Division

(57) ABSTRACT

An imaging apparatus includes a tomographic image acquisition unit configured to acquire a tomographic image indicating a polarization state of a subject based on beams of different polarizations obtained by splitting a beam into which a return beam from the subject irradiated with a measuring beam and a reference beam corresponding to the measuring beam have been combined, and a control unit configured to control an optical path length difference between the return beam and the reference beam according to positional information of a predetermined region in the tomographic image indicating the polarization state of the subject.

12 Claims, 11 Drawing Sheets

(56) References Cited

U.S. PATENT DOCUMENTS

2010/0067020 A1    3/2010   Podoleanu
2011/0237999 A1*   9/2011   Muller et al. .................. 604/20

FOREIGN PATENT DOCUMENTS

WO     2010134624 A1    11/2010
WO     2012/004970 A1    1/2012

* cited by examiner

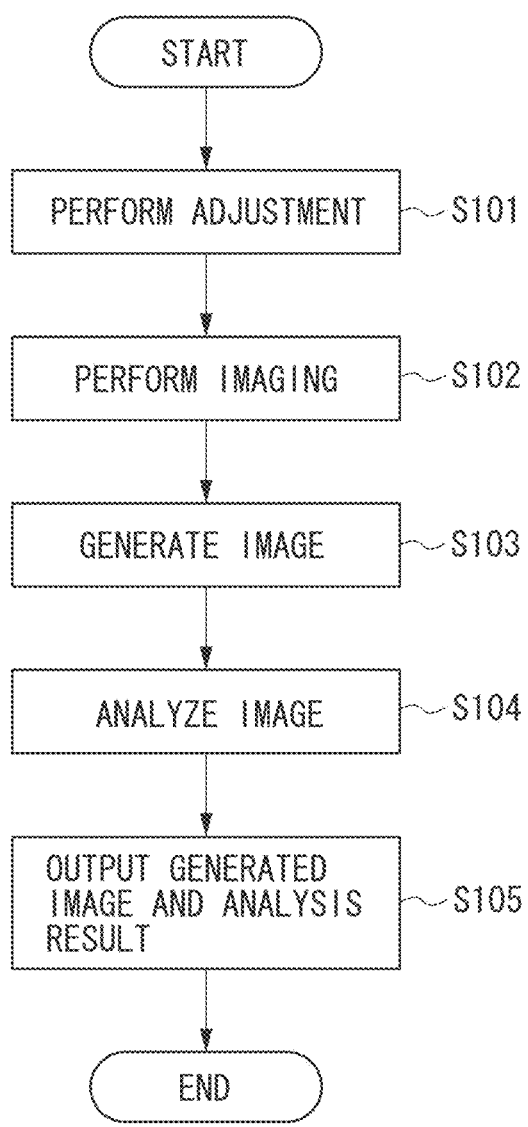

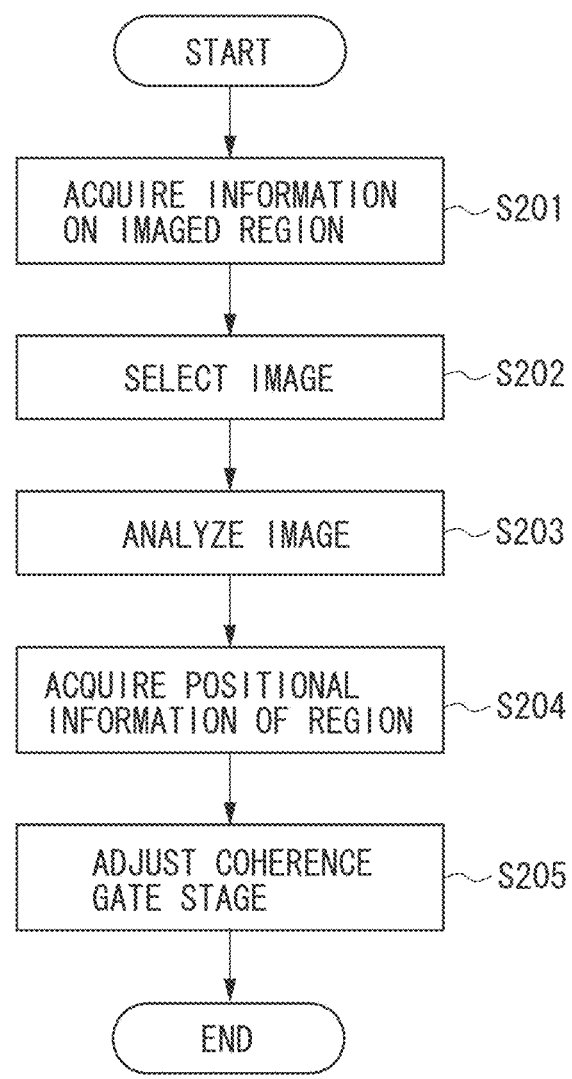

IMAGING APPARATUS, IMAGING METHOD, AND STORAGE MEDIUM

BACKGROUND OF THE INVENTION

1. Field of the Invention

The present invention relates to acquisition of a tomographic image using interference of light. In particular, the present invention relates to a technique for adjusting the position of a coherence gate.

2. Description of the Related Art

An optical coherence tomography (OCT) technique using interference of multi-wavelength light enables acquisition of a high-resolution tomographic image of a sample, such as a human eye.

An OCT apparatus acquires the images of a subject's eye, an internal organ employing an endoscope, and the skin. Further, in recent years, there have been attempts to acquire, using the OCT apparatus, an OCT image that indicates optical characteristics and movement of a fundus tissue in addition to a normal OCT image representing the shape of the fundus tissue.

International Publication No. WO 2010/122118 A1 discusses a polarization sensitive OCT, which is an example of the OCT. The polarization sensitive OCT employs, as a measuring beam for examining the sample, a light beam that has been modulated to a circularly-polarized beam. Detection is then performed by splitting the interference beam into two linearly-polarized beams perpendicular to each other, so that the polarization sensitive OCT image is generated.

Further, there has been an understanding that the polarization sensitive OCT is capable of acquiring different types of information from the conventional OCT, and clinical research is being conducted therein.

When the subject is imaged using OCT, adjustment of an optical path length difference by positioning the coherent gate becomes crucial.

However, there are cases where elements configuring the subject cannot be extracted by only using the conventional OCT image information. In such a case, positioning of the coherent gate for imaging such elements may become troublesome.

SUMMARY OF THE INVENTION

The present invention is direct to a method for appropriately adjusting the position of a coherent gate.

According to an aspect of the present invention, an imaging apparatus includes a tomographic image acquisition unit configured to acquire a tomographic image indicating a polarization state of a subject based on beams of different polarizations obtained by splitting a beam into which a return beam from the subject irradiated with a measuring beam and a reference beam corresponding to the measuring beam have been combined, and a control unit configured to control an optical path length difference between the return beam and the reference beam according to positional information of a predetermined region in the tomographic image indicating the polarization state of the subject.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 3 is a flowchart illustrating a process according to the present exemplary embodiment.

FIG. 4 is a flowchart illustrating a process for adjusting the optical path length.

DESCRIPTION OF THE EMBODIMENTS

Various exemplary embodiments, features, and aspects of the invention will be described in detail below with reference to the drawings.

Figure 1:
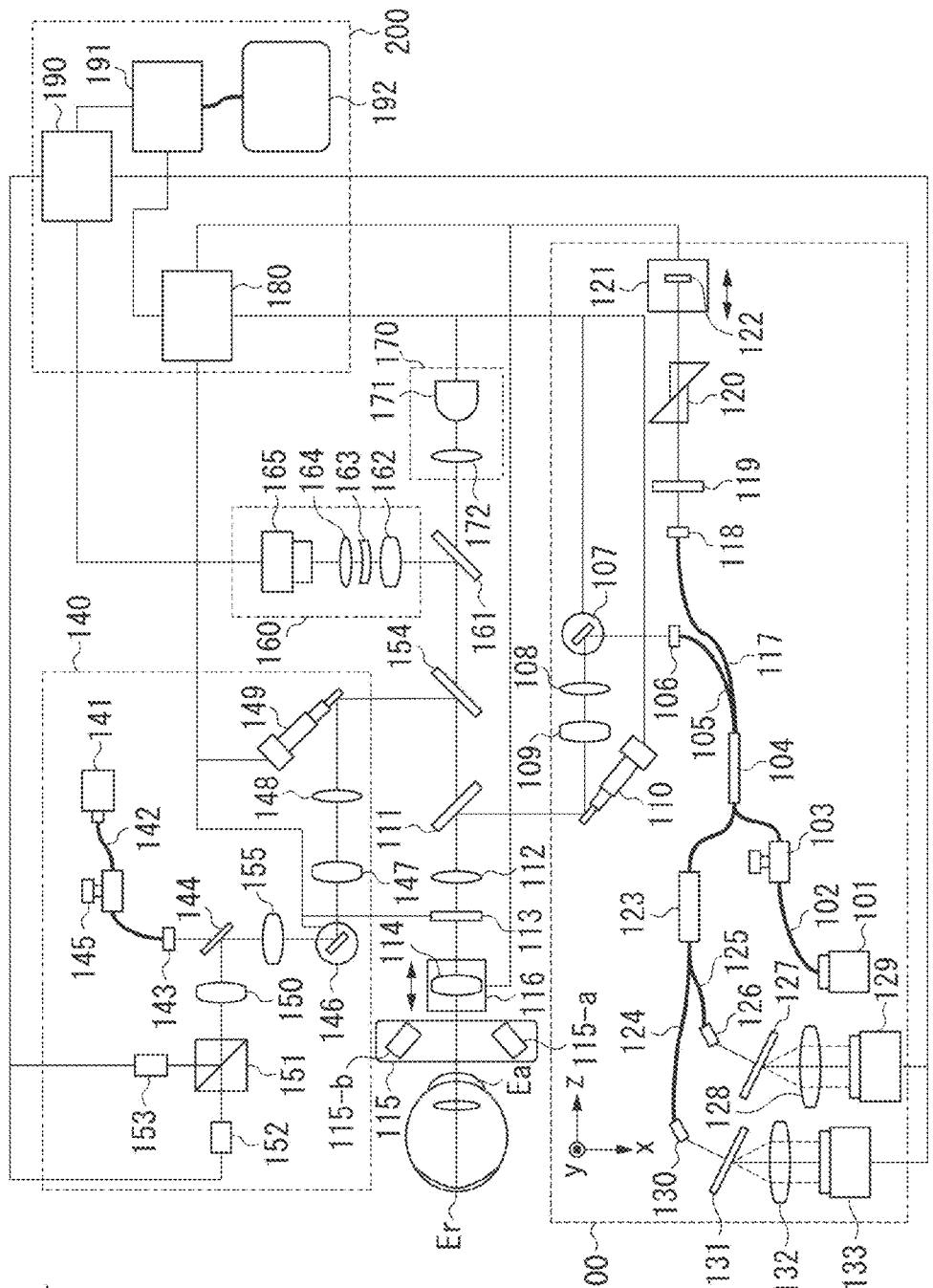
FIG. 1 is a schematic diagram illustrating an imaging apparatus according to an exemplary embodiment of the present invention.

FIG. 1 is a schematic diagram illustrating an imaging apparatus according to an exemplary embodiment of the present invention.

Referring to FIG. 1, the imaging apparatus includes a polarization sensitive OCT (PS-OCT) 100, a polarization sensitive scanning laser ophthalmoscope (PS-SLO) 140, an anterior segment imaging unit 160, an internal fixation lamp 170, and a control unit 200.

The imaging apparatus is aligned by lighting and causing the subject's eye to gaze at the internal fixation lamp 170, and using the image of the anterior segment of the subject captured by the anterior segment imaging unit 160. After completing the alignment, the PS-OCT 100 and the PS-SLO 140 perform imaging of the fundus.

The configuration of the PS-OCT 100 will be described below.

A light source 101, which is a super luminescent diode (SLD), i.e., a low-coherent light source, emits light having a central wavelength of 850 nm and a bandwidth of 50 nm. According to the present exemplary embodiment, the SLD light source is employed as the light source 101. However, any light source that can emit low coherent light, such as an amplified spontaneous emission (ASE) light source, may be used as the light source 101.

The light emitted from the light source 101 is guided by a polarization maintaining (PM) fiber 102 and a polarization controller 103 to a fiber coupler 104 having a polarization preserving function. The light beam is then split into a measuring beam (i.e., an OCT measuring beam) and a reference beam (i.e., a reference beam corresponding to the OCT measuring beam).

The polarization controller 103 adjusts the polarization state of the beam emitted from the light source 101, and adjusts the beam to a linearly-polarized beam. A branching ratio of the fiber coupler 104 is 90 (reference beam):10 (measuring beam).

The measuring beam is output from a collimator 106 via a PM fiber 105 as a parallel beam. The output measuring beam reaches a dichroic mirror 111 via an X scanner 107, lenses 108 and 109, and a Y scanner 110. The X scanner 107 includes a galvano mirror that scans the measuring beam in a horizontal direction on a fundus Er, and the Y scanner 110 includes the galvano mirror that scans the measuring beam in a vertical direction on the fundus Er. The X scanner 107 and the Y scanner 110 are controlled by a drive control unit 180, and are capable of scanning the measuring beam in a desired range on the fundus Er (i.e., an acquisition range of the tomographic image, an acquisition position of the tomographic image, and an irradiation position of the measuring beam). The dichroic mirror 111 reflects light having wavelengths of 800 nm to 900 nm, and transmits light of other wavelengths.

The measuring beam reflected by the dichroic mirror 111 passes, via a lens 112, through a $\lambda/4$ polarizing plate 113 (i.e., an example of a polarization adjustment member) arranged to be inclined at an angle of 45°. The phase of the beam is thus shifted by 90°, and is polarized to a circularly-polarized beam. It is desirable for the inclination of the $\lambda/4$ polarizing plate 113 to be an angle (i.e., an example of an arrangement state) corresponding to an inclination from an optical axis of a polarizing beam splitting surface of a fiber coupler 123 that includes a polarizing beam splitter.

Further, it is desirable to enable the $\lambda/4$ polarizing plate 113 to be inserted and removed from the optical path. For example, the $\lambda/4$ polarizing plate 113 may be mechanically configured to rotate around the optical axis or an axis parallel to the optical axis as the rotational axis. As a result, a compact apparatus capable of easily switching between the SLO optical system and the PS-SLO optical system can be realized. Further, a compact apparatus capable of easily switching between the OCT optical system and the PS-OCT optical system can be realized.

The beam incident on the subject's eye is thus polarized to a circularly-polarized beam as a result of arranging the $\lambda/4$ polarizing plate 113 to be inclined at an angle of 45°. However, the beam may not become a circularly-polarized beam on the fundus Er due to the characteristic of the subject's eye. To solve such a problem, the drive control unit 180 can perform control to finely adjust the inclination of the $\lambda/4$ polarizing plate 113.

A focus lens 114 mounted on a stage 116 focuses, on retinal layers in the fundus Er via an anterior segment Ea of the subject's eye, the measuring beam polarized to a circularly-polarized beam. The measuring beam irradiating the fundus Er is reflected and scattered by each retinal layer, and returns to the fiber coupler 104 via the above-described optical path.

On the other hand, the reference beam split by the fiber coupler 104 is output as a parallel beam from a collimator 118 via a PM fiber 117. The output reference beam is polarized by a $\lambda/4$ polarizing plate 119 arranged to be inclined at an angle of 22.5° from P-polarization similarly as the measuring beam. The reference beam is reflected via a dispersion compensation glass 120 by a mirror 122 mounted on a coherence gate stage 121, and returns to the fiber coupler 104. The reference beam passes through the $\lambda/4$ polarizing plate 119 twice, so that the linearly-polarized beam is returned to the fiber coupler 104.

The coherence gate stage 121 is controlled by the drive control unit 180 to deal with differences in axial lengths of the subject's eye.

The return beam and the reference beam that have returned to the fiber coupler 104 are combined into an interference beam (also referred to as a combined beam). The interference beam becomes incident on the fiber coupler 123 including the polarizing beam splitter, and is split at the branching ratio of 50:50 into beams of different polarization directions (i.e., a P-polarized beam and an S-polarized beam according to the present exemplary embodiment).

The P-polarized beam is dispersed by a grating 131 via a PM fiber 124 and a collimator 130, and is received by a lens 132 and a second line sensor 133. The S-polarized beam is similarly dispersed by a grating 127 via a PM fiber 125 and a collimator 126, and is received by a lens 128 and a first line sensor 129. The gratings 127 and 131 and the line sensors 129 and 133 are arranged to conform to respective polarization directions.

The beams received by the respective line sensors 129 and 133 are output as electrical signals according to the light intensity. The signal processing unit 190 (i.e., an example of a tomographic image generation unit) then receives the output electrical signals.

The inclination of the $\lambda/4$ polarizing plate 113 is adjusted based on the inclination of the polarizing beam splitter. The inclination of the $\lambda/4$ polarizing plate 113 can also be adjusted with respect to a straight line connecting centers of an optic disk and a macula lutea in the fundus. Further, a similar result can be acquired by adjusting the polarized beam splitter and the $\lambda/4$ polarizing plates 113 and 119 based on the vertical direction as a polarization basis.

The configuration of the PS-SLO 140 will be described below.

According to the present exemplary embodiment, a light source 141, i.e., a semiconductor laser, emits a light beam having a central wavelength of 780 nm. The measuring beam (also referred to as an SLO measuring beam) emitted from the light source 141 is polarized via a PM fiber 142 by a polarizing controller 145 to a linearly-polarized beam, and is output from a collimator 143 as a parallel beam. The output measuring beam then passes through a perforated portion of a perforated mirror 144, and reaches via a lens 155, a dichroic mirror 154 via an X scanner 146, lenses 147 and 148, and a Y scanner 149. The X scanner 146 includes a galvano mirror that scans the measuring beam in the horizontal direction on the fundus Er, and the Y scanner 149 includes a galvano mirror that scans the measuring beam in the vertical direction on the fundus Er. The X scanner 146 and the Y scanner 149 are controlled by the drive control unit 180, and are capable of scanning the measuring beam in the desired range on the fundus Er. The dichroic mirror 154 reflects light having wavelengths of 760 nm to 800 nm, and transmits light of other wavelengths.

The linearly-polarized measuring beam reflected by the dichroic mirror 154 reaches the fundus Er via the optical path similar to that of the PS-OCT 100.

The measuring beam irradiating the fundus Er is reflected and scattered by the fundus Er, and reaches the perforated mirror 144 via the above-described optical path. The beam reflected by the perforated mirror 144 is then split by a polarizing beam splitter 151 via the lens 150 into beams of different polarization directions (i.e., a P-polarized beam and an S-polarized beam according to the present exemplary embodiment). The split beams are received by avalanche photodiodes (APD) 152 and 153, converted into electrical signals, and received by the signal processing unit 190 (i.e., an example of the fundus image generation unit).

The position of the perforated mirror 144 is conjugate with the position of the pupil in the subject's eye. The perforated mirror 144 reflects the light that has passed through a peripheral region of the pupil among the light reflected and scattered by the fundus Er irradiated with the measuring beam.

According to the present exemplary embodiment, both the PS-OCT and the PS-SLO use the PM fiber. However, a similar configuration and effect may be acquired by using a single mode fiber (SMF) in the case where the polarizing controller controls polarization.

The anterior segment imaging unit 160 will be described below.

The anterior segment imaging unit 160 irradiates the anterior segment Ea using an irradiation light source 115 including light emitting diodes (LED) 115-a and 115-b, which emit irradiation light having a wavelength of 1000 nm. The light reflected by the anterior segment Ea reaches a dichroic mirror 161 via the lens 114, the polarizing plate 113, the lens 112, and the dichroic mirrors 111 and 154. The dichroic mirror 161 reflects light having wavelengths of 980 nm to 1100 nm, and transmits light of other wavelengths. The light reflected by the dichroic mirror 161 is then received by an anterior segment camera 165 via lenses 162, 163, and 164. The light received by the anterior segment camera 165 is converted into electrical signal and is received by the signal processing unit 190.

The internal fixation lamp 170 will be described below.

The internal fixation lamp 170 includes an internal fixation lamp display unit 171 and a lens 172. A plurality of LEDs arranged in a matrix shape is used as the internal fixation lamp display unit 171. The drive control unit 180 performs control to change a lighting position of the LEDs according to a region to be imaged. The light emitted from the internal fixation lamp display unit 171 is guided to the subject's eye via the lens 172. The internal fixation lamp display unit 171 emits light having a wavelength of 520 nm, and displays a desired pattern by control of the drive control unit 180.

A control unit 200 for controlling the entire apparatus according to the present exemplary embodiment will be described below.

The control unit 200 includes the drive control unit 180, the signal processing unit 190, a display control unit 191, and a display unit 192.

The drive control unit 180 controls each unit as described above.

The signal processing unit 190 generates images based on the signals output from the line sensors 129 and 133, the APD 152 and 153, and the anterior segment camera 165, analyzes the generated images, and generates visualization information of the analysis results. The image generation process will be described in detail below.

The display control unit 191 displays, on a display screen in the display unit 192 (e.g., a liquid crystal display), the images generated by a tomographic image generation unit and a fundus image generation unit. Such images are acquired by a fundus image acquisition unit (not illustrated) and a tomographic image acquisition unit (not illustrated). The image data generated by the signal processing unit 190 may be transmitted to the display control unit 191 via wired or wireless communication. Further, according to the present exemplary embodiment, the imaging apparatus is described above. However, according to another exemplary embodiment of the present invention, the imaging apparatus may be an ophthalmologic apparatus or an ophthalmologic system in which the fundus image acquisition unit includes the SLO optical system and the tomographic image acquisition unit includes the OCT optical system.

The display unit 192 displays display forms indicating various types of information to be described below based on control performed by the display control unit 191. Image data from the display control unit 191 may be transmitted to the display unit 192 via wired or wireless communication. Further, the display unit 192 is included in the control unit 200. However, it is not limited thereto, and the display unit 192 may be separated from the control unit 200. Furthermore, a tablet, which is an example of a portable device, configured by integrating the display control unit 191 and the display unit 192 may be used. In such a case, it is desirable to include a touch panel function in the display unit, so that a user can operate the touch panel to move the display position of the images, enlarge and reduce the images, and change the images to be displayed.

Image generation and image analysis processes performed in the signal processing unit 190 will be described below.

The signal processing unit 190 performs, on interference signals output from the respective line sensors 129 and 133, reconfiguration processing employed in a general spectral domain (SD-) OCT. The signal processing unit 190 thus generates two tomographic images based on respective polarization components (i.e., a tomographic image corresponding to a first polarized beam and a tomographic image corresponding to a second polarized beam).

More specifically, the signal processing unit 190 cancels fixed pattern noise from the interference signals. The signal processing unit 190 cancels the fixed pattern noise by averaging a plurality of A-scan signals that has been detected and thus extracting the fixed pattern noise, and subtracting the extracted fixed pattern noise from the input interference signal.

The signal processing unit 190 then transforms the wavelength of the interference signal to a wave number, performs Fourier transform, and generates a tomographic signal (i.e., a tomographic signal indicating a polarization state).

The signal processing unit 190 performs the above-described process for the interference signals of the two polarization components, and thus generates two tomographic images.

Further, the signal processing unit 190 aligns the signals output from the APD 152 and 153 in synchronization with driving of the X scanner 146 and the Y scanner 149. The signal processing unit 190 thus generates two fundus images based on the respective polarization components (i.e., a fundus image corresponding to the first polarized beam and a fundus image corresponding to the second polarized beam).

Furthermore, the signal processing unit 190 generates an intensity image from the above-described two tomographic signals.

More specifically, the intensity image is basically the same as the tomographic image in the conventional OCT. A pixel value r of the intensity image is calculated from tomographic signals $A_H$ and $A_V$ acquired from each of the line sensors (also referred to as line cameras) 129 and 133 using equation (1).

$$r = \sqrt{A_H^2 + A_V^2} \qquad (1)$$

Moreover, the signal processing unit 190 similarly generates a fundus intensity image from the two fundus images.

Figure 2A:
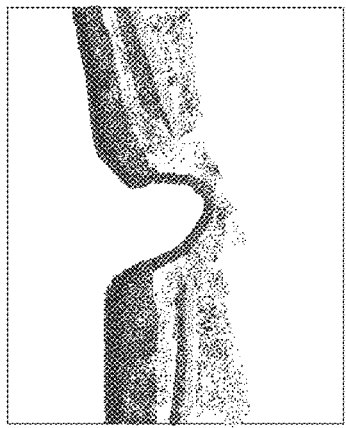
FIGS. 2A, 2B, 2C, 2D, and 2E illustrate examples of images generated by a signal processing unit.

FIG. 2A illustrates an example of the intensity image of the optic disk.

A fiber coupler (not illustrated) arranged between the optical paths of the fiber coupler 104 and the fiber coupler 123 may be used to split the beam, so that the intensity image can be directly generated via the collimators, the gratings, the lenses and the line sensors.

Further, the signal processing unit 190 generates a retardation image from the tomographic images of the polarization components that are perpendicular to each other.

More specifically, a value δ of each pixel in the retardation image is a numerical conversion of a phase difference delay between the vertical and horizontal polarization components at the position of each pixel configuring the tomographic image. The value δ is calculated from each of the tomographic signals $A_H$ and $A_V$ using equation (2).

$$\delta = \arctan\left[\frac{A_V}{A_H}\right] \quad (2)$$

Figure 2C:
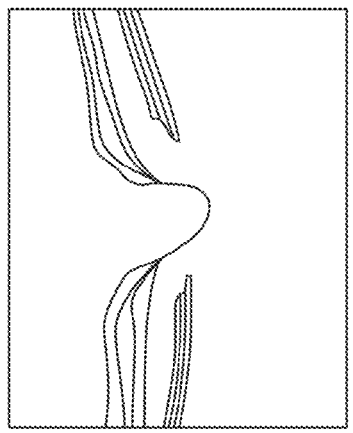
Figure 2B:

FIG. 2B illustrates an example of the retardation image of the optic disk generated as described above. The retardation image can be acquired by calculating equation (2) for each B-scan image. As described above, the retardation image is a tomographic image indicating the difference of the effect received by the two polarized beams at the subject's eye. Referring to FIG. 2B, the values indicating the above-described ratio are displayed as a color tomographic image. A darker-shaded portion indicates that the value of the ratio is small, and a lighter-shaded portion indicates that the value of the ratio is large. As a result, generating the retardation image enables recognizing a layer in which there is birefringence. For further details, refer to "E. Gotzinger et al., Opt. Express 13, 10217, 2005".

The signal processing unit 190 generates a retardation map from the retardation images acquired with respect to a plurality of B-scan images.

More specifically, the signal processing unit 190 detects a retinal pigment epithelium (RPE) in each B-scan image. Since the RPE scrambles the polarization state of light, the signal processing unit 190 searches for a retardation distribution of each A-scan along the depth direction in the range from an inner limiting membrane (ILM) and not including the RPE. The signal processing unit 190 then sets a maximum value of the retardation as a representative value of the retardation in the A-scan.

The signal processing unit 190 performs the above-described process on all retardation images, and thus generates the retardation map.

FIG. 2C illustrates an example of the retardation map of the optic disk. Referring to FIG. 2C, the darker-shaded portion indicates that the phase difference is small, and the lighter-shaded portion indicates that the phase difference is large. The layer having birefringence in the optic disk is a retinal nerve fiber layer (RNFL), and the retardation map illustrates the phase difference caused by the birefringence in the RNFL and the thickness of the RNFL. As a result, the phase difference becomes large where the RNFL is thick, and becomes small where the RNFL is thin. The thickness of the RNFL for the entire fundus thus becomes recognizable using the retardation map, so that the retardation map can be used in diagnosis of glaucoma.

The signal processing unit 190 performs linear approximation of the value of the retardation δ in the range of the ILM to the RNFL in each A-scan image of the previously generated retardation image. The signal processing unit 190 then determines the acquired slope as the birefringence at the position on the retina in the A-scan image. The signal processing unit 190 performs the above-described process on all of the acquired retardation images, and generates the map representing the birefringence.

In other words, since retardation is a product of a distance and the birefringence in the RNFL, a linear relation is acquired by plotting the depth and the value of the retardation in each A-scan image. As a result, the slope acquired by performing linear approximation of the plot using a least-square method becomes the value of the birefringence in the RNFL in the A-scan image.

Figure 2D:
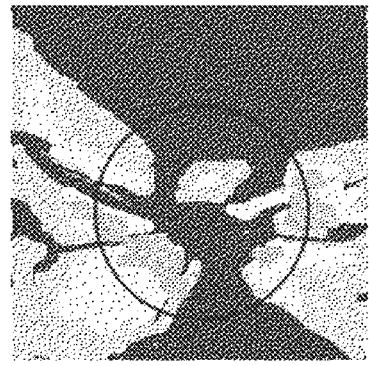

FIG. 2D illustrates an example of the birefringence map of the optic disk. The birefringence map directly maps the values of the birefringence so that, even if a fibrous architecture of the RNFL changes when the thickness of the RNFL does not change, the change can be visualized as the change in the birefringence.

The signal processing unit 190 then calculates a Stokes vector S for each pixel from the acquired tomographic signals $A_H$ and $A_V$, and a phase difference $\Delta\Phi$ between the tomographic signals $A_H$ and $A_V$, using equation (3).

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\Phi \\ 2A_H A_V \sin\Delta\Phi \end{pmatrix} \quad (3)$$

$\Delta\Phi$ is calculated from phases $\Phi_H$ and $\Phi_V$ of each signal acquired when calculating the two tomographic images, as $\Delta\Phi = \Phi_V - \Phi_H$.

The signal processing unit 190 then sets, in each B-scan image, a window of the size that is proximately 70 μm in a main scanning direction of the measuring beam and 18 μm in a depth direction. The signal processing unit 190 averages each element of the Stokes vector calculated for each pixel by a number C within each window, and calculates a degree of polarization uniformity (DOPU) within the window using equation (4).

$$\text{DOPU} = \sqrt{Q_m^2 + U_m^2 + V_m^2} \quad (4)$$

Figure 2E:
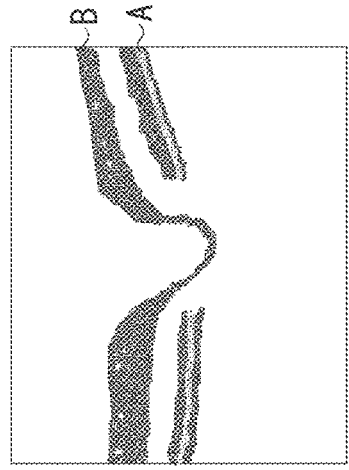

In equation (4), $Q_m$, $U_m$, and $V_m$ are values acquired by averaging the elements Q, U, and V in the Stokes vector within each window. The signal processing unit 190 performs the above-described process for all windows in the B-scan images, and generates a DOPU image (i.e., a tomographic image indicating the degree of polarization uniformity) of the optic disk as illustrated in FIG. 2E.

DOPU is a value indicating the uniformity of polarization, and becomes close to "1" when the polarization state is preserved, and smaller than "1" when the polarization state is scrambled or not preserved. Since the RPE in the structure of the retina scrambles the polarization state of light, the value of the DOPU in the portion corresponding to the RPE in the DOPU image becomes lower than the values in the other portions. Referring to FIG. 2E, the lighter-shaded portion indicates the RPE. The DOPU image visualizes the layer such as the RPE that scrambles the polarization state of light, so that the RPE can be more clearly imaged as compared to using a change in the intensity, even when the RPE is deformed due to a disease.

According to the present exemplary embodiment, the above-described tomographic images corresponding to the first and second polarized beams, the retardation image, and the DOPU image will be referred to as the tomographic images indicating the polarization state. Further, according to the present exemplary embodiment, the above-described retardation map and the birefringence map will also be referred to as the fundus images indicating the polarization state.

The signal processing unit 190 uses the above-described intensity image to perform segmentation of the tomographic image.

More specifically, the signal processing unit 190 applies, to the tomographic image to be processed, a median filter and a Sobel filter respectively and generates respective images (hereinafter referred to as a median image and a Sobel image). The signal processing unit 190 then generates a profile for each A-scan from the generated median image and Sobel image. The signal processing unit 190 generates the profile of intensity values from the median image and the profile of gradients from the Sobel image. The signal processing unit 190 detects peaks in the profiles generated from the Sobel image. Further, the signal processing unit 190 refers to the profiles of the median image corresponding to regions before and after the detected peaks and the regions between the detected peaks, and extracts a boundary of each region in the retinal layers.

Further, the signal processing unit 190 measures each layer thickness in the direction of the A-scan line, and generates a layer thickness map of each layer.

The operation performed by the imaging apparatus according to the present exemplary embodiment will be described below.

FIG. 3 is a flowchart illustrating the operation performed by the imaging apparatus according to the present exemplary embodiment. FIG. 4 is a flowchart illustrating an adjustment process illustrated in FIG. 3.

In step S101 illustrated in FIG. 3, the imaging apparatus and the subject's eye positioned on the imaging apparatus are aligned. The process unique to the present exemplary embodiment with respect to performing alignment will be described below. Since alignment of a working distance in X, Y, and Z directions, focusing, and adjustment of the coherence gate are general processes, descriptions will be omitted.

Figure 5:
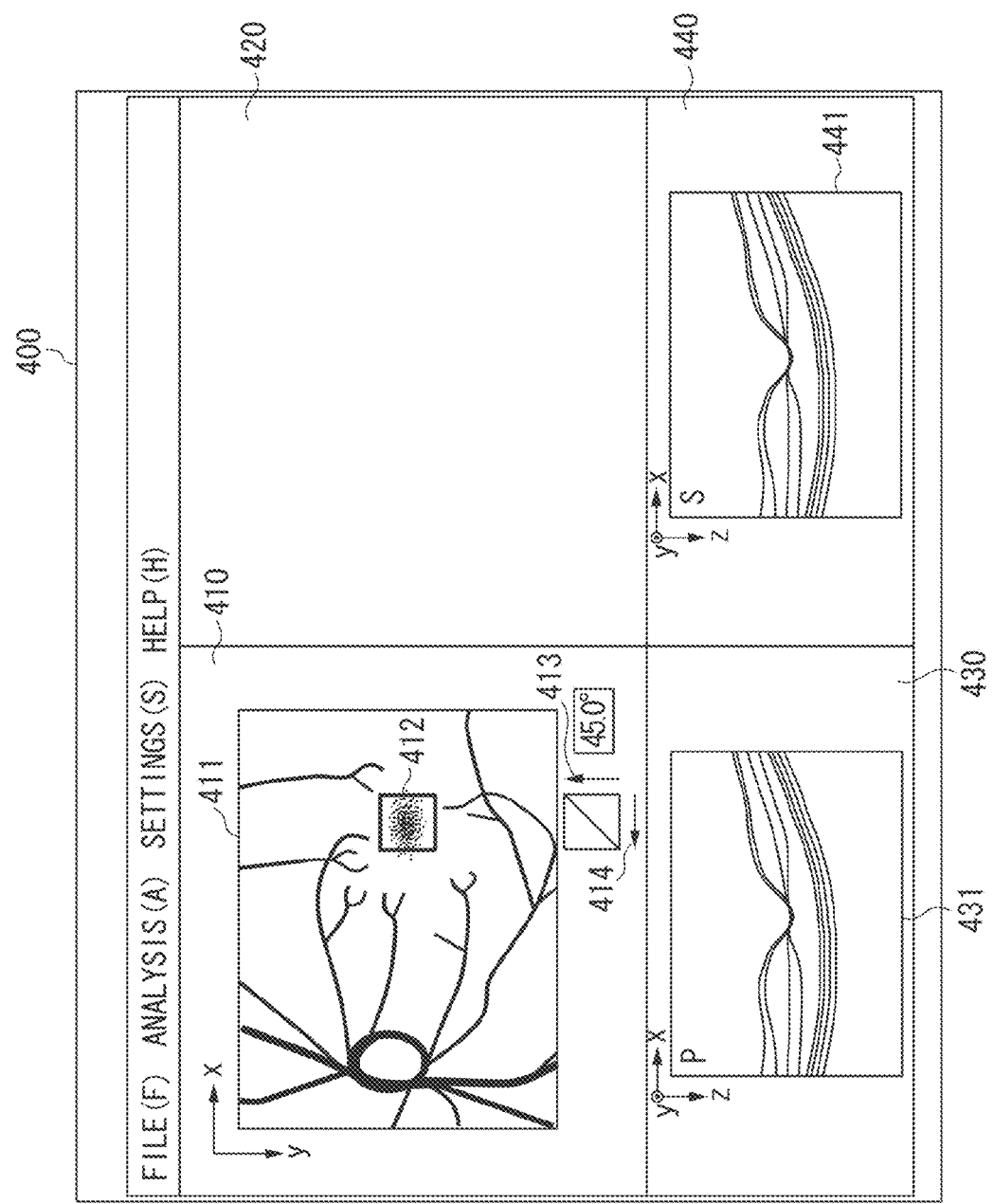
FIG. 5 illustrates a display example of a display screen on a display unit in the imaging apparatus according to the present exemplary embodiment.

FIG. 5 illustrates a window 400 displayed on the display unit 192 when performing adjustment. Referring to FIG. 5, a display area 410 (i.e., an example of a first display area) displays a fundus image 411 (i.e., an intensity fundus image or a two-dimensional fundus image) imaged by the PS-SLO 140 and generated by the signal processing unit 190. A frame 412 indicating an imaging range (i.e., an acquisition range or an acquisition position) of the PS-OCT 100 is superimposed on the fundus image 411.

An operator sets an imaging range under control of the drive control unit 180 by clicking and dragging an instruction device (not illustrated), such as a mouse, and designating by a cursor displayed on the window. In other words, the operator designates the frame 412 using the cursor, and moves the frame 412 by the dragging operation. As a result, the drive control unit 180 controls a drive angle of a scanner and sets the imaging range. According to the present exemplary embodiment, the mouse includes a sensor for detecting a movement signal when the user manually moves the mouse in two directions, left and right mouse buttons for detecting that the user has pressed the button, and a wheel mechanism between the two mouse buttons which is movable in front and back and left to right directions. Further, the display unit may include a touch panel function, and the operator may designate the acquisition position on the touch panel.

The control unit 200 drives a coherence gate stage 121 according to a tomographic signal indicating the polarization state to adjust the coherence gate.

In other words, the control unit 200 adjusts the coherence gate by adjusting the optical path length differences of the subject to be measured.

In step S201 illustrated in FIG. 4, the control unit 200, which also functions as a selection unit, acquires information on an imaging region. In step S202, the control unit 200 selects, based on the acquired information, the retardation image or the DOPU image, i.e., the tomographic image indicating the polarization state, to be used in adjusting the coherence gate. For example, if the imaging region includes the RPE as an anatomic region, the control unit 200 selects the DOPU image.

In step S203, the control unit 200 detects, by performing the above-described method, signal intensities corresponding to the RPE, i.e., the layer which scrambles the polarization state of light, and to the retinal layers in the DOPU image.

Since the value of the RPE is significantly small as compared to the other layers in the DOPU image, the RPE and the other layers can be distinguished by setting a threshold value. The threshold value may be experimentally-obtained. In the case of a retina of a human eye, if a value range of the DOPU image is normalized from "0" to "1", it is desirable to set the threshold value between approximately 0.5 and 0.7. Further, it is desirable to exclude the region in the intensity image in which an intensity level is extremely low, such as a vitreum. The control unit 200 identifies, as the RPE, the region in which the value of the DOPU image is within the above-described range and the value of the intensity image is of a predetermined level. As a result, the tomographic image indicating the polarization state can be divided into the RPE indicated as "A" and inner membrane layers other than the RPE indicated as "B" illustrated in FIG. 2E.

In step S204, the control unit 200 acquires the positional information of the detected RPE. In step S205, the control unit 200 drives the coherence gate stage 121 based on the positional information of the RPE, so that the predetermined retinal layer is at a desired position in the generated tomographic image.

More specifically, the control unit 200 performs control so that the detected RPE is as close as possible to the coherence gate within the imaging range, and the inner membrane layers do not spread out to a field of view. On the other hand, if the subject has a disease, such as age-related macular degeneration, and the RPE is damaged, the control unit 200 may adjust the coherence gate stage 121 so that the signal of the inner membrane layers indicated as "B" illustrated in FIG. 2E is at a predetermined position instead of the RPE. In such a case, if the length or the area of the RPE detected in the DOPU image is less than the predetermined value, the control unit 200 uses the inner membrane layers instead of the RPE. Further, disease information of the subject's eye may be stored in a storage device (not illustrated) attached to the control unit 200. When the subject's eye is to be re-examined, the control unit 200 may then read, from the storage device, the disease information and select the retinal layer to be used in adjusting the coherence gate stage 121.

Furthermore, if a nerve fiber layer or a sclera is to be a region of interest, the control unit 200 adjusts the coherence gate using the retardation image instead of the DOPU image. In such a case, since the layer having birefringence such as the nerve fiber layer and the sclera is stressed, the control unit 200 adjusts the coherence gate based on such a layer.

The sclera is a membrane located on the outermost layer, and minute morphological changes are less likely to occur unlike the inner membrane layers, so that the sclera is a more robust region of interest in adjusting the coherence gate. The coherence gate can thus be adjusted with respect to the entire retinal layer region to be used in the diagnosis, by using the DOPU image for the inner membrane layers and a sclera signal detected from the retardation image for the sclera. Further, since the coherence gate can be adjusted by focusing on a plurality of different layers, the coherent gate can be adjusted based on the layer with less damage even when the retinal layer is deformed due to the disease.

The automatic adjustment of the coherence gate is as described above. The coherence gate stage 121 may also be manually adjusted as follows. The adjustment screen illustrated in FIG. 5 displays, on a display area 430 or 440, either the DOPU image or the retardation image, i.e., the tomographic image indicating the polarization state. The operator then operates the cursor using the mouse while viewing the image. In such a case, the operator can similarly confirm the region which was not visible in the tomographic image of conventional intensity information, so that the coherence gate can be accurately adjusted.

The adjustment of the λ/4 polarizing plate 113 will be described below.

Referring to FIG. 5, indicators 413 and 414 are displayed for adjusting the angle of the λ/4 polarizing plate 113. The user instructs using the instruction device, adjustment of the angle of the λ/4 polarizing plate 113 under control of the drive control unit 180. The indicator 413 is for instructing adjustment in a counterclockwise direction, and the indicator 414 is for instructing adjustment in a clockwise direction. A numerical value displayed besides the indicators 413 and 414 indicates the current angle of the λ/4 polarizing plate 113.

The operator gives, using the cursor by operating on the mouse, an instruction so that the intensities of the tomographic images of each polarized beam respectively displayed on the display area 430 (i.e., a third display area) and the display area 440 (i.e., a fourth display area) become the same. A peak intensity value may be displayed along with tomographic images 431 and 441 (i.e., the tomographic images corresponding to the first polarized beam and the second polarized beam respectively) of the respective polarized beams, or waveforms of respective interference signals may be directly displayed. The operator thus performs adjustment while viewing the peak intensity value or the waveform. It is desirable to display a display form indicating the type of each image (e.g., a letter "P" indicating the P-polarized beam and a letter "S" indicating the S-polarized beam) superimposed on the tomographic images 431 and 441 of the respective polarized beams (or tomographic images 531 and 541 to be described below). As a result, the user can be prevented from misrecognizing the image. The letters may be displayed above or besides the image instead of being superimposed on the image, as long as the display is arranged to be associated with the image.

Further, it is not necessary at this point for a display area 420 (i.e., a second display area) to display any information. If adjustment is to be automatically performed, a display form indicating the current adjustment state (e.g., a message indicating "adjusting λ/4 polarizing plate") may be displayed on the display area 420. Furthermore, the window 400 may display a display form indicating patient information such as a left eye or a right eye, or image capturing information such as an image capturing mode.

It is desirable that adjustment is performed in the following order: alignment adjustment using the anterior segment image (or a luminescent spot in a cornea); focus adjustment using the fundus image indicating the polarization state; coherence gate adjustment using the tomographic image indicating the polarization state; and adjustment of the λ/4 polarizing plate. Further, it is desirable to determine the acquisition position of the tomographic image indicating the polarization state before adjusting the coherence gate using the tomographic image indicating the polarization state. However, it may be determined in the initial settings to acquire a center region of the funcus image indicating the polarization state. Adjustment can then be easily performed to accurately acquire the tomographic image indicating the polarization state that is finer and of a narrower range as compared to the fundus image indicating the polarization state. In such a case, the λ/4 polarizing plate may be automatically adjusted in response to completion of adjustment of the coherence gate, or in response to an input of a signal for acquiring the image indicating the polarization state. Further, the λ/4 polarizing plate may be previously adjusted on an initial setting screen when the ophthalmologic apparatus is activated, so that the λ/4 polarizing plate is not required to be adjusted for each image capturing.

Furthermore, if the λ/4 polarizing plate can be inserted and removed with respect to the optical path, it is desirable that adjustment is adjusted in the following order: alignment adjustment using the anterior segment image (or the luminescent spot in the cornea); focus adjustment using the SLO fundus image; coherence gate adjustment using the OCT tomographic image; and adjustment of the λ/4 polarizing plate after inserting the λ/4 polarizing plate in the optical path. Adjustment before acquiring the image indicating the polarization state can thus be performed using the normal SLO fundus image and the OCT tomographic image the user is intuitively used to. The coherence gate may also be adjusted using the tomographic image indicating the polarization state of the PS-OCT by inserting the λ/4 polarizing plate after performing focus adjustment. In such a case, the λ/4 polarizing plate may be automatically inserted in the optical path in response to completion of adjustment of the coherence gate, or in response to an input of the signal for acquiring the image indicating the polarization state.

Moreover, the focus may be finely adjusted using the OCT tomographic image after coarsely adjusting the focus using the SLO fundus image.

Further, the above-described adjustments may be automatically performed in the above-described order, or by the user adjusting the cursor to a slider corresponding to each type of adjustment displayed on the display unit and performing dragging. Furthermore, if the λ/4 polarizing plate is to be inserted or removed, an icon instructing inserting or removing the λ/4 polarizing plate with respect to the optical path may be displayed on the display unit.

In step S102, step S103, and step S104 illustrated in FIG. 3, the light sources 101 and 141 emit the respective measuring beams. The line sensors 129 and 133 and the APD 152 and 153 then receive the return beam, and the signal processing unit 190 generates and analyzes each image as described above.

The process for outputting the generated image and the analysis result performed in step S105 will be described below.

After the signal processing unit 190 completes generating and analyzing each image, the display control unit 191 generates output information based on the result. The display control unit 191 then outputs to and displays on the display unit 192 the output information.

Figure 6:
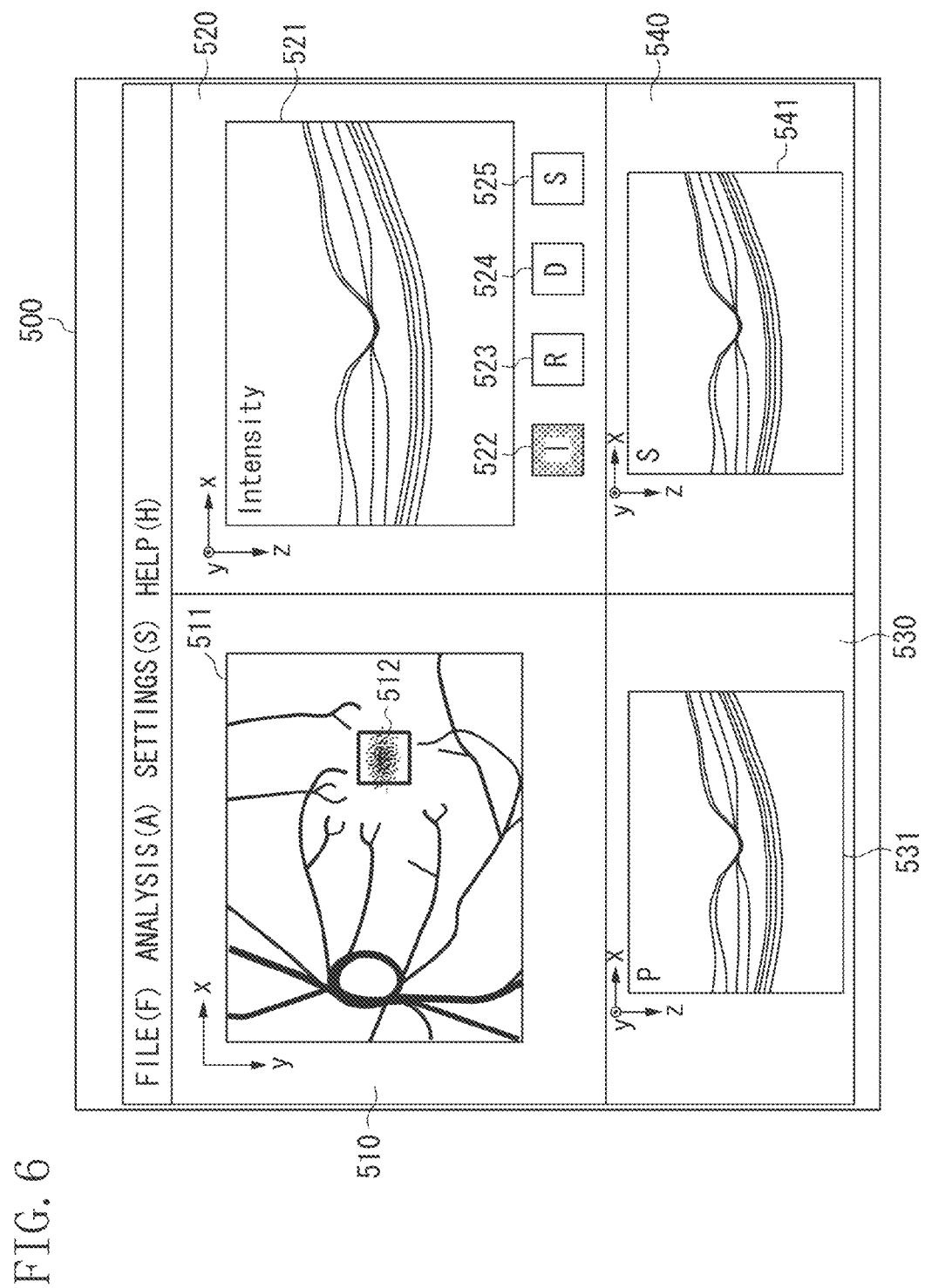
FIG. 6 illustrates a display example of the display screen on the display unit in the imaging apparatus according to the present exemplary embodiment.

FIG. 6 illustrates a display example on the display unit 192 according to the present exemplary embodiment.

Referring to FIG. 6, a window 500 displayed on the display unit 192 includes display areas 510, 520, 530, and 540.

The display area 510 (i.e., the first display area) displays a fundus image 511, and a rectangular frame 512 indicating the position of the tomographic image is superimposed on the fundus image 511. The fundus intensity image is displayed as the fundus image 511. However, the fundus image may be generated based on a polarization signal.

The display area 520 (i.e., the second display area) displays a tomographic image (i.e., an intensity tomographic image) 521. Further, the display area 520 displays buttons 522, 523, 524, and 525 (i.e., an example of the selection unit) for selecting the type of the tomographic image to be displayed. The user may select the type of the tomographic image from a menu instead of using the buttons 522, 523, 524, and 525. In the example illustrated in FIG. 6, the user has selected the button 522.

The display area 530 (i.e., a third display area) and the display area 540 (i.e., a fourth display area) respectively display tomographic images 531 and 541 based on each polarization signal used in generating the tomographic image 521. The display areas 530 and 540 may also display the respective fundus images based on each polarization signal from which the fundus image (i.e., intensity fundus image) displayed on the display area 510 has been generated, according to an instruction from the operator via the menu.

It is desirable to display the intensity tomographic image 521, and a retardation image 621 and a DOPU image 721 to be described below, by superimposing the display form indicating the type of the image (e.g., "intensity", "retardation", and "DOPU", in characters). As a result, the user can be prevented from misrecognizing the image. The type of image may be displayed above or besides the image instead of being superimposed on the image, as long as the characters are arranged to be associated with the image.

Figure 7:
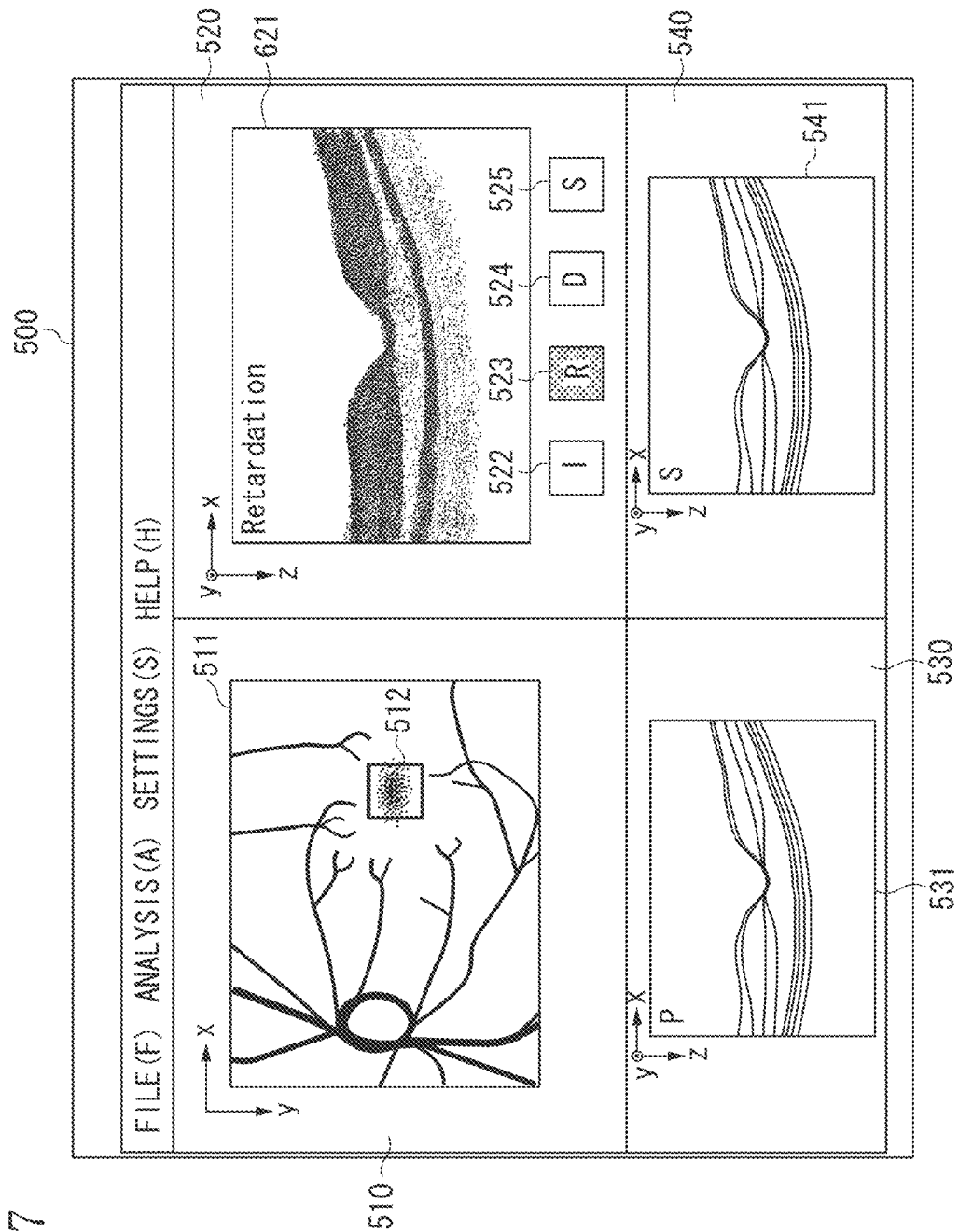
FIG. 7 illustrates a display example of the display screen on the display unit in the imaging apparatus according to the present exemplary embodiment.

If the operator presses the button 523, the tomographic image displayed on the display area 520 can be changed to a retardation image 621 as illustrated in FIG. 7.

Referring to FIG. 7, the display areas 530 and 540 respectively display the tomographic images 531 and 541 similarly as in FIG. 6.

Figure 8:
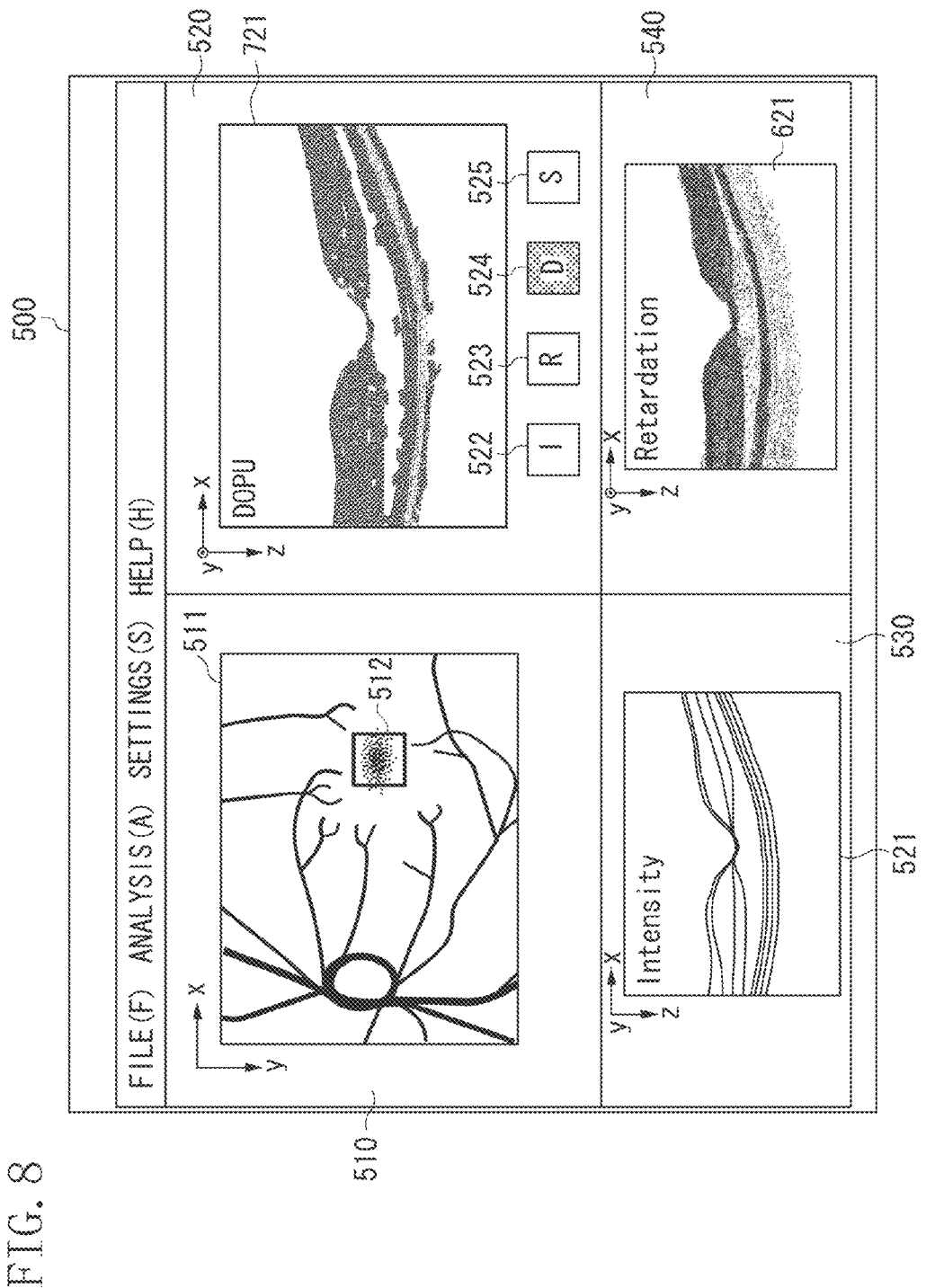
FIG. 8 illustrates a display example of the display screen on the display unit in the imaging apparatus according to the present exemplary embodiment.

If the operator then presses the button 524, the tomographic image displayed on the display area 520 can be changed to a DOPU image 721 as illustrated in FIG. 8.

Referring to FIG. 8, the display area 530 displays the intensity image 521, and the display area 540 displays the retardation image 621. It is desirable to provide a button for selecting the image for each display area. The user thus becomes capable of easily selecting the images to be compared (e.g., a plurality of tomographic images indicating different polarization states).

Figure 9:
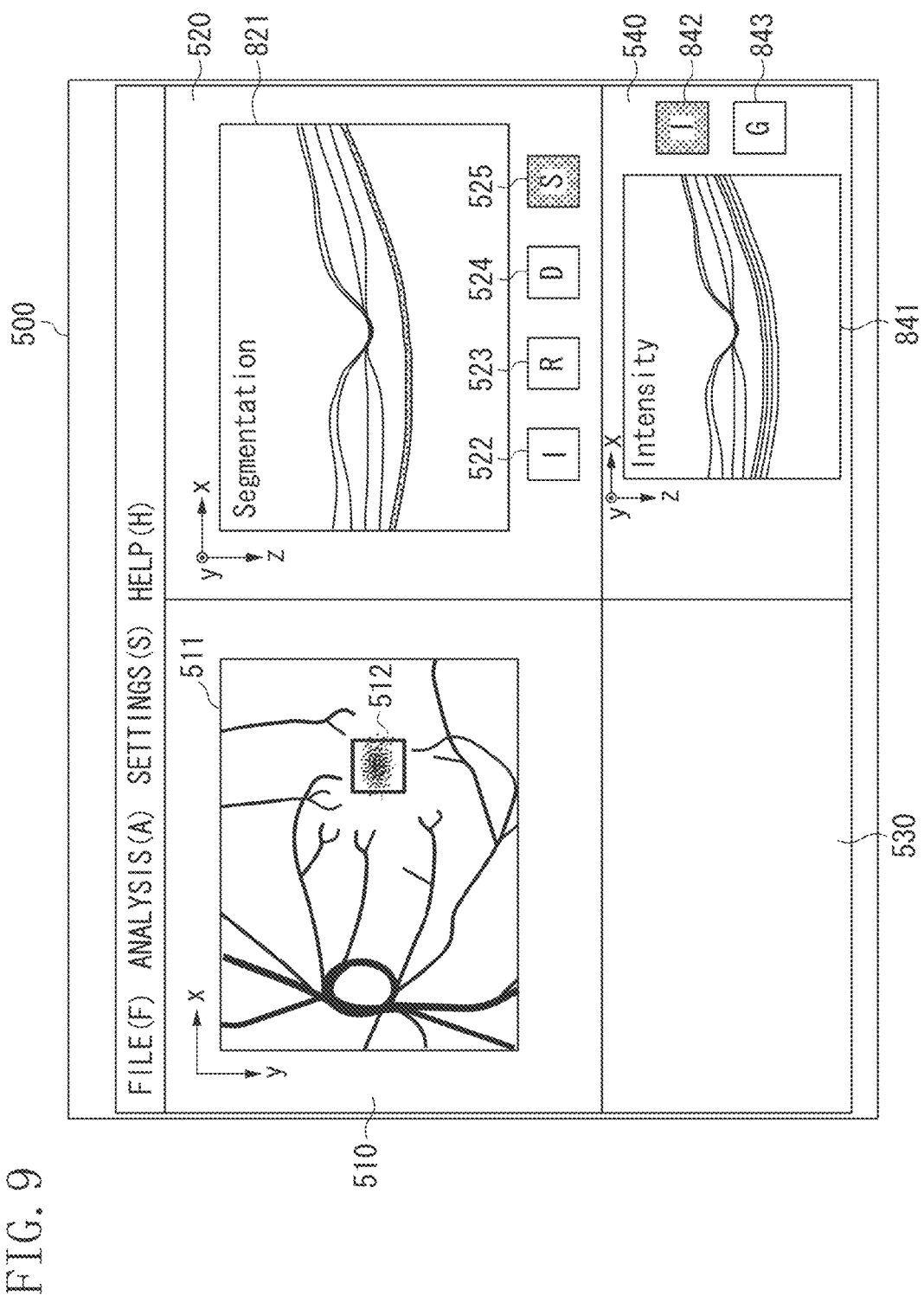
FIG. 9 illustrates a display example of the display screen on the display unit in the imaging apparatus according to the present exemplary embodiment.

If the operator presses the button 525, the tomographic image displayed on the display area 520 can be changed to an image 821 indicating a segmentation result as illustrated in FIG. 9. Referring to FIG. 9, color line segments indicating layer boundaries are superimposed on the tomographic image and displayed in the image 821, and the RPE is highlighted. The layer selected by the operator using the cursor is highlighted.

The display area 540 displays a tomographic image (i.e., intensity image) 841 used in performing segmentation, and buttons 842 and 843. If the operator presses the buttons 842 and 843, the intensity image 841 can be switched to a graph 941, illustrated in FIG. 10, indicating the layer thickness of the highlighted layer.

Figure 10:
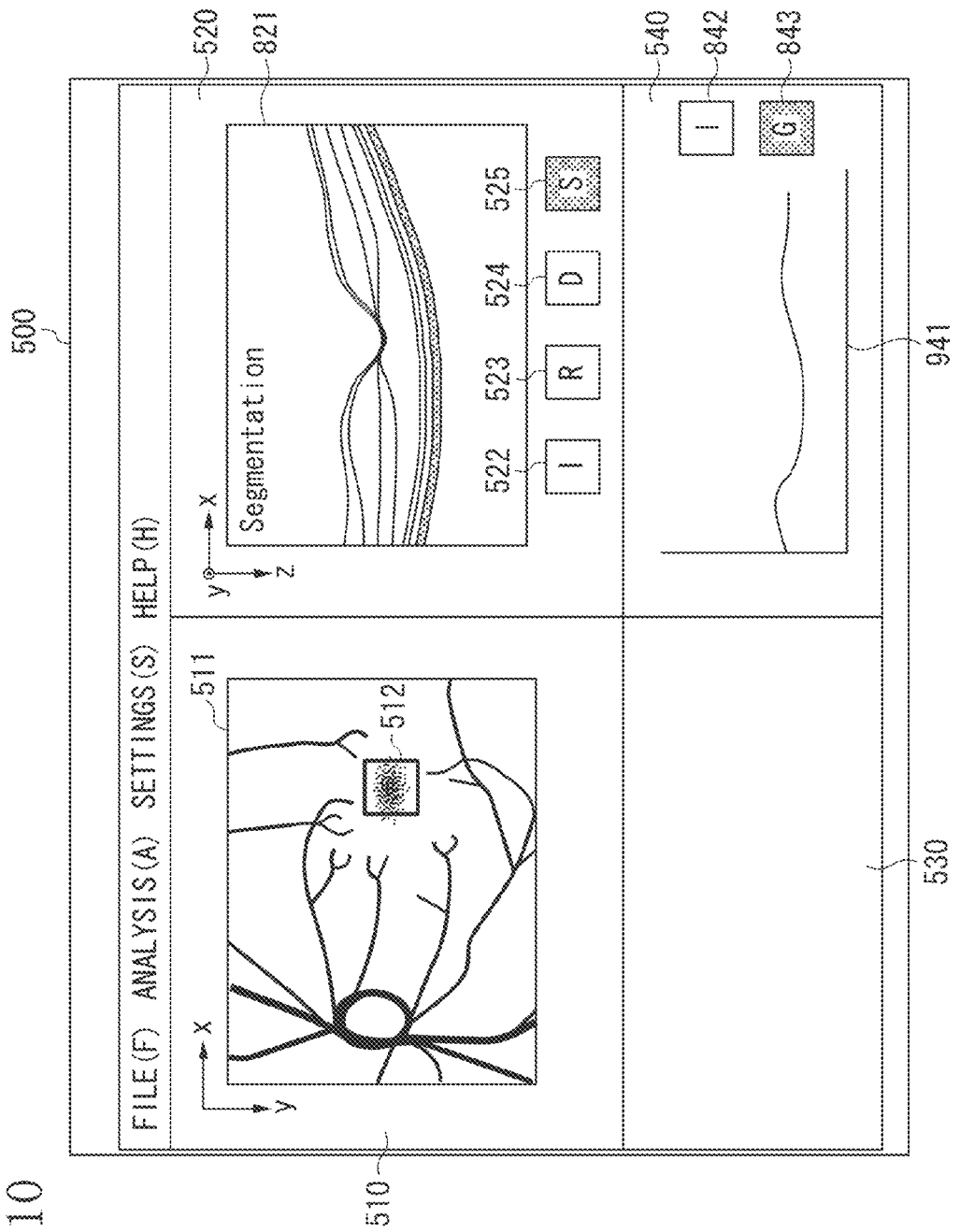
FIG. 10 illustrates a display example of the display screen on the display unit in the imaging apparatus according to the present exemplary embodiment.
Figure 11:
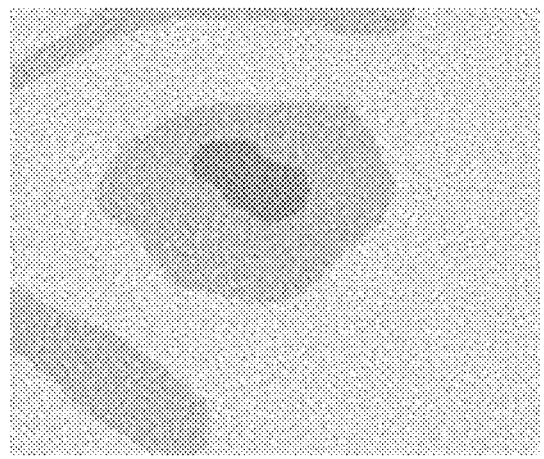
FIG. 11 illustrates an example of a two-dimensional layer thickness map displayed on the display unit in the imaging apparatus according to the present exemplary embodiment.

Further, referring to FIG. 10, thickness information of the selected layer (e.g., a two-dimensional layer thickness map as illustrated in FIG. 11) may be displayed on the display area 530. Referring to FIG. 11, the thickness of the selected layer is expressed by a difference in color. An integration image (i.e., an integration image generated based on a specific layer or on the entire PS-OCT) may be displayed in place of the thickness of the selected layer illustrated in FIG. 11. Further, according to the present exemplary embodiment, the image to be displayed is changed based on the instruction from the operator. However, the operator may select information on the disease to be diagnosed (e.g., the name of the disease) from the menu, so that the image on which a priority order has been preset with respect to the disease is displayed on each display area.

As described above, according to the present exemplary embodiment, each of the generated images can be efficiently presented to the operator.

Further, the operator can select the necessary images with easy operation. In particular, the operation becomes easier by previously associating the name of the disease with the image to be displayed.

Furthermore, polarization adjustment of the measuring beam can be easily performed.

According to the present exemplary embodiment, the positions of the display areas in which the above-described images are displayed are not limited thereto. For example, the fundus image may be displayed in the left display area in the display screen. Further, the number of images to be displayed is not limited thereto. For example, the fundus image and the tomographic image (i.e., two images) may be displayed side by side on the display screen when performing adjustment. The display method may then be changed after performing image capturing, and a plurality of tomographic images indicating different polarization states may be displayed side by side on the display screen along with the fundus image. Furthermore, the order and the positions in which the buttons 522, 523, 524, and 525 are arranged are not limited thereto.

The present exemplary embodiment is directed to ophthalmology. However, the present invention may be easily applied to the endoscope and the skin by those skilled in the art.

Further, the present invention may be realized by supplying, to a system or an apparatus via a network or various storage media, software (a program code) for implementing functions of the above-described exemplary embodiments, and a computer (or a central processing unit (CPU) or a micro-processing unit (MPU)) of the system or the apparatus can read and execute the program code.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2012-010278 filed Jan. 20, 2012, which is hereby incorporated by reference herein in its entirety.

What is claimed is:

1. An imaging apparatus comprising:
    a tomographic image acquisition unit configured to acquire a tomographic image indicating a polarization state of a return beam from a subject based on beams of different polarization states obtained by combining the return beam from the subject and a reference beam; and
    a control unit configured to control an optical path length difference between the return beam and the reference beam according to positional information of a predetermined fundus layer in the tomographic image indicating the polarization state,
    wherein the predetermined fundus layer is the layer that scrambles the polarization state of a beam or the layer having birefringence.

2. The imaging apparatus according to claim 1, wherein the tomographic image is one of a first tomographic image indicating information on a phase difference between the beams of different polarizations and a second tomographic image indicating a degree of polarization uniformity between the beams of different polarizations.

3. The imaging apparatus according to claim 1, wherein the tomographic image acquisition unit further acquires a tomographic image as intensity information acquired based on the optical path length difference controlled by the control unit, and
wherein the imaging apparatus further comprises a display control unit configured to display the tomographic image as the intensity information.

4. The imaging apparatus according to claim 1, further comprising an analysis unit configured to perform segmentation of retinal layers included in the tomographic image indicating the polarization state,
wherein the control unit controls the optical path length difference based on positional information of the predetermined fundus layers acquired by the segmentation performed by the analysis unit.

5. The imaging apparatus according to claim 1, wherein the imaging apparatus forms both a first tomographic image indicating information on a phase difference between the beams of different polarization states and a second tomographic image indicating a degree of polarization uniformity between the beams of different polarization states,
wherein the imaging apparatus further comprises a selection unit configured to select one of the first tomographic image and the second tomographic image, and
wherein the control unit controls the optical path length difference based on the selected tomographic image.

6. The imaging apparatus according to claim 5, wherein the selection unit selects the first tomographic image in a case where the subject includes a birefringence, region.

7. The imaging apparatus according to claim 5, wherein the selection unit selects the first tomographic image in a case where the subject includes a nerve fiber layer, a sclera, or a cornea.

8. The imaging apparatus according to claim 5, wherein the selection unit selects the second tomographic image in a case where the subject includes a retinal pigment epithelium.

9. An imaging method comprising:
acquiring a tomographic image indicating a polarization state of a return beam from subject based on beams of different polarization states obtained by combining the return beam from the subject and a reference beam; and
controlling an optical path length difference between the return beam and the reference beam according to positional information of a predetermined fundus layer in the tomographic image indicating the polarization state,
wherein the predetermined fundus layer is the layer that scrambles the polarization state of a beam or the layer having birefringence.

10. A computer-readable storage medium storing a program that causes a computer to execute the imaging method according to claim 9.

11. An imaging apparatus comprising:
a light source;
a first unit configured to split light emitted from the light source to a measuring beam and a reference beam;
a combining unit configured to combine a return beam from a subject irradiated with the measuring beam and a return beam from a mirror irradiated with the reference beam into a combined beam;
a second unit configured to split the combined beam into beams of different polarization directions;
a tomographic image acquisition unit configured to acquire, based on beams of different polarizations obtained by the second unit performing splitting, a tomographic image indicating a polarization state of the return beam from the subject; and
a control unit configured to control a position of the mirror according to positional information of a predetermined fundus layer in the tomographic image,
wherein the predetermined fundus layer is the layer that scrambles the polarization state of a beam or the layer having birefringence.

12. An imaging apparatus configured to acquire a tomographic image of a subject, the imaging apparatus comprising:
a light source;
a first fiber coupler configured to split light emitted from the light source into a measuring beam and a reference beam;
a mirror configured to reflect the reference beam;
a second fiber coupler configured to combine a return beam from a subject irradiated with the measuring beam and the reference beam reflected by the mirror into a combined beam;
a third fiber coupler configured to split the combined beam into a first beam and a second beam of different polarization directions;
a first line sensor configured to convert the first beam to an electrical signal;
a second line sensor configured to convert the second beam to an electrical signal;
a signal processing unit configured to acquire, based on the electrical signals converted by the first line sensor and the second line sensor, a tomographic image indicating a polarization state of the return beam from the subject; and
a control unit configured to control a position of the mirror according to positional information of a predetermined fundus layer in the tomographic image,
wherein the predetermined fundus layer is the layer that scrambles the polarization state of a beam or the layer having birefringence.

* * * * *